United States Patent [19]

Rabinoff

[11] Patent Number: 5,508,271
[45] Date of Patent: Apr. 16, 1996

[54] TREATMENT OF NEUROLOGICAL DYSFUNCTION WITH METHYLCOBALAMIN

[75] Inventor: Michael Rabinoff, Biddeford, Me.

[73] Assignee: Biogenesys, Wilmington, Del.

[21] Appl. No.: 88,459

[22] Filed: Jul. 7, 1993

[51] Int. Cl.$^6$ .......................... A61K 31/70; A61K 33/24; A61K 31/40; C07H 19/23
[52] U.S. Cl. .......................... 514/52; 514/561; 536/26.44; 562/559
[58] Field of Search .......................... 562/559; 536/26.4, 536/26.44, 27.31; 514/46, 81, 260, 561, 52

[56] References Cited

U.S. PATENT DOCUMENTS 5,137,712   8/1992   Kask et al. .................................. 424/10

OTHER PUBLICATIONS

Kieburtz et al., "Abnormal Vitamin $B_{12}$ Metabolism in Human Immunodeficiency Virus Infection", *Arch. Neurol.*, 48:312–314 (1991).
Pfohl et al., "Effect of Cobalamin Derivatives on in Vitro Enzymatic DNA Methylation: Methylcobalamin Can Act as a Methyl Donor", *Biochemistry*, 30(32):8045–8051 (1991).
Sakane et al., "Effects of Methyl–$B_{12}$ on the in Vitro Immune Functions of Human T Lymphocytes", *J. of Clin. Immunology*, 2(2):101–109 (1982).
Scott and Weir, "Hypothesis: The Methyl Folate Trap", *The Lancet*, Aug. 15, pp. 337–340 (1981).
Surtees et al., "Association of Demyelination with Deficiency of Cerebrospinal–fluid S–adenosylmethionine in Inborn Errors of Methyl–transfer Pathway", *The Lancet*, 338:1550–1554 (1991).
Surtees et al., "Central–nervous–system Methyl–group Metabolism in Children with Neurological Complications of HIV Infection", *The Lancet*, 335:619–621 (1990).
Yaqub et al., "Effects of Methylcobalamin on Diabetic Neuropathy", *Clinical Neurology and Neurosurgery*, 94:105–111 (1992).

*Primary Examiner*—Gary L. Kunz
*Attorney, Agent, or Firm*—Bertram I. Rowland; Pamela J. Sherwood

[57] ABSTRACT

A method for treating neurological dysfunctions associated with AIDS or ARC comprising the administration of methylcobalamin, alone or in combination with methionine. Substantial increases in the number of T4+ T-lymphocytes, T8+ T-lymphocytes, or the ratio of T4+ to T8+ T-lymphocytes is also observed with this treatment.

2 Claims, No Drawings

TREATMENT OF NEUROLOGICAL DYSFUNCTION WITH METHYLCOBALAMIN

TECHNICAL FIELD

The field of this invention is the treatment of neurological and immunological disorders which may arise in a mammalian host as the result of imbalances in methyl group metabolism.

BACKGROUND

The mammalian immune system is very complex; and disorder in its regulation may affect other organs in a number of ways. Lymphocytes and macrophages may directly attack cells of the body. Various metabolic products of these cells may be deleterious to tissue. Antibodies against autoantigens can accumulate in the kidneys and joints.

Several neurological disorders are thought to have an autoimmune component. In animal models for multiple sclerosis, T lymphocytes reactive with myelin basic protein can trigger disease symptoms. HIV infection is well known to have various neuropathies associated with it, where the degeneration of neural cells and demyelination may be directly caused by the action of cells in the immune system.

HIV infected patients with neurological disorders have increased neopterin levels in cerebrospinal fluid, possibly as a result of γ-interferon leading to increased synthesis of neopterin in monocytes and macrophages. Excess production of dihydroneopterin may lead to folate deficiency causing demyelination in the brain. Indolamine-2,3-dioxygenase activity is also increased by exposure to γ-interferon, leading to increased conversion of tryptophan to various metabolites, including quinolonic acid, which is neurotoxic.

Neural cells are sensitive to deficiencies in methyl group metabolism. At the present time there is not a definitive answer as to why this happens, although a number of theories have been postulated. The major pathway for methylation in humans is through S-adenosylmethionine (SAM). The immediate precursor to SAM is methionine, which is produced by a pathway where 5-methyltetrahydrofolate transfers a methyl group to cobalamin, forming methylcobalamin, which in turn methylates homocysteine to form methionine. The cycling of homocysteine to methionine is required to maintain methylation homeostasis. It is possible that myelin basic protein is particularly unstable when there is a methionine deficiency. SAM is also required for the biosynthesis of phospholipids, which are required for neural function.

In the treatment of neurological disorders with methyl-donor compounds to restore normal methyl-group metabolism, it is beneficial to the host to use compounds which can positively affect the underlying immune disorder.

RELEVANT LITERATURE

A review of the metabolic pathways for methylation, particularly those that function through S-adenosyl-methionine, can be found in Pfohl-Leszkowicz, et al. (1991) Biochemistry 30:8045–8051, *Effect of cobalamin derivatives on in vitro enzymatic DNA methylation: methylcobalamin can act as a methyl donor.* The effects of a deficiency in components of this pathway is discussed in J. Scott, et al. (1981) The Lancet Aug. 15, pp. 337–340, The methyl folate trap.

Surtees, et al. (1991) The Lancet 338:1550–1554, *Association of demyelination with deficiency of cerebrospinal-fluid S-adenosylmethionine in inborn errors of metabolism* discusses the treatment of methylation deficiencies for genetic defects.

Deficiencies of Vitamin $B_{12}$ metabolism in HIV patients is discussed in Kieburtz, et al. (1991) Arch Neur. 48:312–314, *Abnormal Vitamin $B_{12}$ metabolism in Human Immunodeficiency Virus Infection, association with neurological dysfunction.* Surtees, et al. (1990) The Lancet 335:619–621, *Central-nervous-system methyl-group metabolism in children with neurological complications of HIV infection* discusses the effect of methylation deficiencies in HIV infected children.

Sakane, et al. (1982) J. Clin. Immunol. 2:101–109, discusses the effect of methylcobalamin on T lymphocytes in vitro. Yaqub, et al. (1992) Clinical Neurology and Neurosurgery 94:105–111 determines the effect of methylcobalamin on diabetic neuropathy.

SUMMARY OF THE INVENTION

The subject invention provides a method for treating a host with neurological dysfunction associated with an immunological disorder, by the administration of a methyl donor compound, particularly methylcobalamin. The methyl donor compounds are also used to restore normal metabolic biochemical functions after immune mediated disruption of biochemical pathways.

DESCRIPTION OF THE SPECIFIC EMBODIMENTS

Methods and compositions are provided for treating neurological dysfunction which may occur in association with an immunological disorder. Methyl donor compounds, or precursors thereof are able to stabilize or reverse neurological symptoms which may occur as a result of immune associated imbalances in methyl group and folate metabolism. The methyl donor compounds are also able to positively affect the regulation of cells in the immune system, as a means of stopping the disease causing process. The improvement in the immune function is a further advantage for the patient.

The methyl donor compounds used in the treatment are those components and metabolites of the pathway which leads to synthesis of S-adenosyl-methionine in the body. Such compounds include 5-methyltetrahydrofolate, methionine, S-adenosylmethionine, adenosylcobalamin, methylcobalamin, methionine, betaine, etc. Of particular interest is methylcobalamin, which has a positive effect on cells of the T lineage.

The compounds are used to treat immunological disorders, such as autoimmune disease, immunodeficiencies which result from infection or immunosuppressive drug treatment, lack of immune response to tumor cells, and the like. The compounds act to potentiate an immune response, increasing proliferation of lymphocytes in response to mitogenic signals and increasing the level of response by the lymphocytes.

Patients for which the subject therapy is indicated include those who are infected with human immunodeficiency virus (HIV). Particularly, HIV infected patients which have developed acquired immune deficiency syndrome (AIDS) or AIDS related complex (ARC) often have neurological complications which can benefit from methyl donor treatment. In a number of patients an increase in the blood concentration of T lymphocytes, particularly T4 positive lymphocytes, is seen after the subject therapy.

Neurological dysfunction which may be treated with the subject compounds include vacuolar myelopathy, demyelination, spasticity, encephalopathy, immune mediated encephalitis, subacute encephalitis, calcification of basal ganglia, numbness of fingers, hands and forearms, breakdown of myelin and disruption of the axon, pain and tingling in feet, distal diminution of sensation, minor motor neuron signs confined to the feet and diminished ankle reflexes, difficulty walking, spasticity in legs, weakness and uncoordinated legs, distal symmetrical polyneuropathy, inflammatory demyelinating polyneuropathy, multiple neuropathy, progressive polyradiculopathy, autonomic neuropathy, and the like. Conditions of particular interest, which are frequently associated with HIV infection, include vacuolar myelopathy, distal symmetrical polyneuropathy and demyelination.

The mammalian host may be a human clinical patient, pet or research animal, including murine and other rodents, lagomorphs, porcine, feline, bovine, canine, primate, etc.

The subject compounds are administered in an amount effective to stabilize or reverse the neurological dysfunction. To further benefit the patient, the dose is sufficient to cause an upregulation in the immune system. This may be manifested as an increase in the number of T4 and/or T8 positive lymphocytes in an HIV infected patient, as an increase in anti-tumor or other T cell mediated activity, an increase in suppresser cells which effect a reduction in autoimmune activity, and the like.

The compounds, 5-methyltetrahydrofolate, methionine, S-adenosylmethionine, adenosylcobalamin, methylcobalamin, methionine, betaine, etc., are administered to a host in a physiologically acceptable carrier.

The compounds may be administered in a variety of ways, orally, parenterally, or by inhalation. For oral administration, the pharmaceutical composition will generally contain from about 5–100% by weight of the active material, for other applications, the composition will generally have from about 0.05–50 wt. % of the active material. For injection, the methyl donor compounds may be injected subcutaneously, intramuscularly, intraperitoneally, intravascularly, etc. Depending upon the manner of introduction, the compounds may be formulated in a variety of ways. Carriers include excipients, sugars, alum, dimethyl sulfoxide, etc. Of particular interest are methods of administration which will target the drug to the nervous system, either by direct injection, site specific drug delivery, prodrugs or carriers that target neural tissue or increase penetration of the blood brain barrier, and the like.

The pharmaceutical compositions can be prepared in various forms, such as granules, tablets, pills, capsules, suspensions, and the like. Pharmaceutical grade organic or inorganic carriers and/or diluents suitable for oral use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The subject compositions will generally be administered from as often as daily for initial treatment, to as infrequently as monthly for maintenance level treatment. The amount may vary with the general health of the patient, the response of the patient to the drug, whether the methyl donor compound is used by itself or in combination with other drugs, and the like. Daily administrations may be one or more times, usually not more than about four times, particularly depending upon the level of drug which is administered.

Methylcobalamin treatment will usually be from 3 times daily to once weekly administration. The preferred method of administration in i.m. injection. Maintenance treatment may be administered monthly. The dose at each administration will usually be from about 0.1 to 10,000 micrograms, more usually from about 1 to 1500 micrograms, preferably from about 100 to 1000 micrograms. Oral administration may be as much as 10,000 milligrams. L-methionine will usually be administered orally. The dosage may be from 1 g/day to as much as 25 g/day, and will usually be from 1 to 10 g/day, more usually from 3 to 9 g/day. Dosage for betaine will be from 25 mg/day to as much as 15 g/day, usually 1 to 5 g/day, more usually about 3 g/day. Dosage for 5 methyltetrahydrofolic acid will be from 100 µg/day to as much as 150 mg/day, and will usually be from 100 µg/day to 25 mg/day, more usually from 500 µg/day to 5 mg/day. Dosage from S-adenosyl-methionine will be from 1 to 1000 mg/day, usually from 10 to 100 mg/day, more usually from 200 to 400 mg/day.

Other drugs which may be used in accordance with conventional treatments for HIV infection or other retroviral infection include AZT, ddI, ddC, oral methionine, steroids, vitamin $B_{12}$, etc. The additional drugs may be administered separately or in conjunction with the methyl donor compounds and may be formulated in the same formulation.

The following examples are offered by way of illustration and not by way of limitation.

EXPERIMENTAL

Ten AIDS patients with associated neurological dysfunction were treated over a three month period with methylcobalamin. Methylcobalamin administration was intramuscular (IM) unless otherwise noted. Plan A gave 1000 micrograms of methylcobalamin every other day for two weeks, then 250 micrograms weekly for a month, then 1000 micrograms per month. Plan B gave 1000 micrograms methylcobalamin weekly for three months. The methylcobalamin was stored at 4° C., and used within 24 hours of dilution. For intramuscular injection the methylcobalamin was dissolved in normal saline, for intravenous injection the methylcobalamin was dissolved in Ringer's or lactated Ringer's solution. Patients were treated with AZT or oral methionine as noted. The results are presented in Table 1.

TABLE 1

| Subject | pre-treatment T4+ cells/mm³ | pre-treatment T8+ cells/mm³ | post-treatment T4+ cells/mm³ | post-treatment T8+ cells/mm³ | Treatment with AZT | Methylcobalamin Treatment | Treatment with oral Methionine | Age of patient | Neurological Symptoms after treatment |
|---|---|---|---|---|---|---|---|---|---|
| 1 | 162 | 716 | 210 | 747 | yes | Plan A | — | 35 | reduction in depressed |

TABLE 1-continued

| | | | | | | | | |
|---|---|---|---|---|---|---|---|---|
| | | | | | IM | | | ankle reflexes, reduction in distal weakness |
| 2 | 197 | 674 | 242 | 698 | no | Plan A IM | — | 32 | reduction in loss of position and vibratory sense reduction in distal weakness |
| 3 | 142 | 705 | 191 | 742 | yes | Plan A IM | 3–9 gm/day | 41 | marked reduction in spasticity, reduction in distal weakness, reduction in loss of position and vibratory sense |
| 4 | 184 | 646 | 235 | 673 | yes | Plan B IM or IV | — | 38 | elimination of pins and needles sensation and muscle weakness |
| 5 | 262 | 722 | 319 | 771 | no | Plan B IM | — | 37 | reduction in loss of position and vibratory sense reduction in distal weakness |
| 6 | 310 | 947 | 335 | 981 | no | Plan B IM | — | 34 | elimination of pins and needles sensation and muscle weakness |
| 7 | 121 | 708 | 167 | 729 | yes | Plan A IM or IV | 3–9 gm/day | 41 | marked reduction in spasticity, reduction in distal weakness |
| 8 | 109 | 669 | 178 | 714 | yes | Plan A IM or IV | 3–9 gm/day | 38 | marked reduction in ataxia, reduction in distal weakness, reduction of loss of position and vibratory sense |
| 9 | 177 | 596 | 251 | 635 | yes | Plan A IM | — | 37 | elimination of pins and needles sensation and muscle weakness |
| 10 | 216 | 648 | 269 | 691 | yes | Plan A IM | — | 40 | reduction in depressed ankle reflexes, reduction in distal weakness |

| | $T4^+$ cells/mm$^3$ | $T8^+$ cells/mm$^3$ | T4/T8 | Statistical Significance |
|---|---|---|---|---|
| Pre-treatment | 188 | 703.1 | 0.267 | Difference in pre- and post-$T4^+$ population; paired, 2 tail T-test; $p < 0.001$ |
| Post-treatment | 239.7 | 738.1 | 0.325 | Difference in pre- and post-$T8^+$ populations; paired, 2 tail T-test; $p < 0.001$ |

Plan A gave 1000 micrograms of methylcobalamin every other day for two weeks, then 250 micrograms weekly for a month, then 1000 micrograms per month.
Plan B gave 1000 micrograms methylcobalamin weekly for three months.
Blood was taken from patients, stained for T4 or T8 surface antigen and the number of lymphocytes counted (columns of $T4^+$ and $T8^+$ cells).

It is evident from the above results, that treatment of patients with AIDS associated neurological dysfunction with methylcobalamin provides for substantial improvements in the patient neurological symptoms, as well as increasing the concentration of T lymphocytes in the blood.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating a person with neurological dysfunction associated with AIDS or ARC selected from the group consisting of depressed ankle reflexes; distal weakness; loss of position and vibratory sense; spasticity; pins and needles sensation; ataxia; and muscle weakness; said method comprising:

administering to a person undergoing AZT treatment, methylcobalamin in an amount effective to stabilize or reverse said neurological dysfunction; and wherein said amount of methylcobalamin is further effective to increase the ratio of T4+T lymphocytes, the blood concentration of T4+ of the blood concentration of T8+T lymphocytes.

2. A method according to claim 1, wherein said methylcobalamin is administered in combination with oral methionine.

* * * * *